United States Patent [19]

Yamashita et al.

[11] 4,380,629

[45] Apr. 19, 1983

[54] STYRYL-LIKE COMPOUNDS SHOWING A COLOR-DEVELOPING AND BLEACHING BEHAVIOR WITH IMPROVED STABILITY AND PROLONGED LIFETIME

[75] Inventors: Akio Yamashita, Machida; Masaaki Hayami, Okayama, both of Japan

[73] Assignee: Matsushita Electric Industrial Company, Limited, Osaka, Japan

[21] Appl. No.: 255,374

[22] Filed: Apr. 20, 1981

[30] Foreign Application Priority Data

Apr. 21, 1980 [JP] Japan .................................. 55-53268

[51] Int. Cl.³ .......................................... C07D 498/04
[52] U.S. Cl. .................................. 542/455; 260/243.3; 260/244.4; 260/245.6; 260/245.7; 260/245.5; 544/32; 544/89; 544/242; 544/333; 546/270; 548/121; 548/159; 548/150; 548/217; 542/401; 542/415; 542/432; 542/434
[58] Field of Search ............... 260/243.3, 244.4, 245.6, 260/245.7, 245.5; 544/32, 89, 242, 333; 546/270; 548/121, 159, 150, 217; 542/415, 401, 432, 434, 455

[56] References Cited

U.S. PATENT DOCUMENTS 3,975,379 8/1976 Schmitt ................................. 542/457
4,147,862 4/1979 Hayami et al. ...................... 542/457
4,314,058 2/1982 Hayami et al. ...................... 542/455

*Primary Examiner*—Arthur P. Demers
*Attorney, Agent, or Firm*—Lowe, King, Price & Becker

[57] ABSTRACT

Styryl-like compounds showing improved stability and prolonged lifetime on repetition of the coloration and bleaching cycle and represented by the general formula

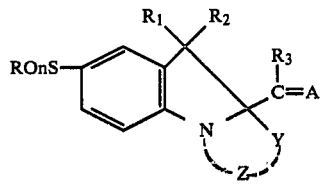

in which R represents an alkyl or phenyl group, $R_1$ and $R_2$ independently represent a lower alkyl group, a hydroxyalkyl group, or an alkoxyalkyl group, $R_3$ represents hydrogen, an alkyl group, a halogen, a nitrile group, an aromatic group or a phenoxy group, Y represents O or S, Z represents an alkylene radical of 2 to 4 carbon atoms, with or without alkyl substituent(s), necessary for forming a ring structure together with

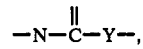

A represents a residue of an aromatic aldehyde, a heterocyclic aldehyde, an aromatic nitroso compound or a heterocyclic nitroso compound, and n is an integer of 2 or 3.

9 Claims, 1 Drawing Figure

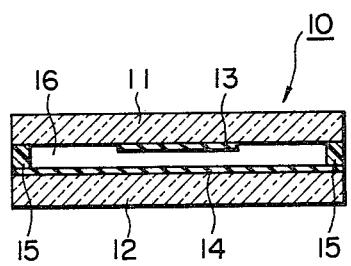

STYRYL-LIKE COMPOUNDS SHOWING A COLOR-DEVELOPING AND BLEACHING BEHAVIOR WITH IMPROVED STABILITY AND PROLONGED LIFETIME

BACKGROUND OF THE INVENTION

1. Field of the Invention

This invention relates to new derivatives of styryl-like compounds with improved stability which undergo color change, coloration or bleaching reversibly or, in some cases, irreversibly in response to external activating energies such as light, heat, ions, electric potential, pressure, radiant rays and so on.

2. Description of the Prior Art

Styryl-like compounds which show a coloring or bleaching or color-changing behavior on application, for example, of electric potential are disclosed in U.S. Pat. No. 4,003,633. These compounds are of the general formula (I)

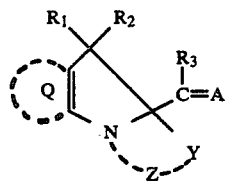

in which Q represents a benzene ring with or without substituents and/or condensed ring(s), $R_1$ and $R_2$ may be the same or different and represent lower an alkyl radical, a hydroxyalkyl radical or an alkoxyalkyl radical, $R_3$ represents hydrogen, an alkyl radical, a halogen, a nitrile radical, an aromatic radical or a phenoxy radical, Y represents O or S, Z represents an alkylene radical or 2 to 4 carbon atoms with or without alkyl substituent(s), necessary to form a ring structure together with

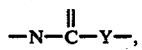

and A represents a condensation reaction residue of an aromatic aldehyde, a heterocyclic aldehyde, an aromatic nitroso compound or heterocyclic nitroso compound.

When external energies are applied to these styryl-like compounds, the chemical structure of the compound is changed reversibly from one to another state, thereby showing color. However, repeated application of external energies shows a tendency that the compounds are deteriorated in quality and are not completely bleached when the external energies have been removed.

SUMMARY OF THE INVENTION

It is accordingly an object of the present invention to provide new derivatives of styryl-like compounds which are stably colored or bleached or color-changed reversibly or irreversibly in response to external activating energies such as light, heat, ions, electric potential, pressure, radiant rays and so on and are thus suitable for use as displaying and recording materials.

It is another object of the invention to provide new derivatives of styryl-like compounds which are more improved in lifetime and stability than the known styryl-like compounds.

The above objects can be achieved by modified styryl-like compounds represented by the following general formula (II)

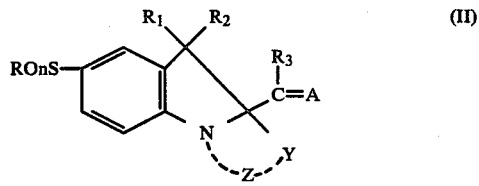

in which $R_1$, $R_2$, $R_3$, A, Y and Z have the same meanings as defined hereinbefore with reference to the formula (I), R represents an alkyl group or phenyl group, and n is an integer of 2 or 3.

In the above formula, the alkyl group for R includes those having 1 to 24 carbon atom and preferably 1 to 8 carbon atom, including methyl, ethyl, propyl, n-butyl and the like. Most preferably, R represents methylsulfonyl or phenylsulfonyl from a view point of economy and solutility in water.

BRIEF DESCRIPTION OF THE DRAWING

A sole FIGURE is a schematic sectional view showing a display device using styryl-like compounds according to the invention.

EMBODIMENTS OF THE INVENTION

The modified styryl-like compound according to the invention can be readily prepared from two starting materials, i.e. indoline derivatives represented by the following formula (III)

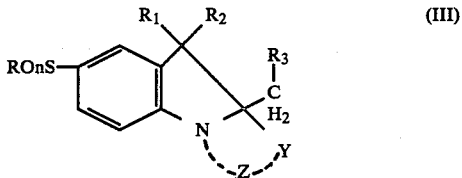

in which R, $R_1$, $R_2$, $R_3$, Y and Z have the same meanings as defined hereinbefore, and aromatic or heterocyclic aldehydes or nitroso compounds. The indoline derivatives can be prepared according to the known, modified Fischer's method and the introduction of the $RO_nS$ group into the benzene ring of the indoline derivative is feasible by converting, for example, a $SOcl_2$ group attached to the benzene ring into a corresponding $RO_2S$ group by two steps using a known technique.

As defined, R represents an alkyl group or a phenyl group. The alkyl group has generally 1 to 24 carbon atoms, and preferably 1 to 8 carbon atoms because of higher synthetic yield of the indolenine nucleus and higher crystallinity of final products. That is, the alkyl group having 1 to 8 carbon atoms is preferable in view of easy in preparation of indoline derivatives, high yield and inexpensive cost for starting materials.

The reaction between the indoline derivatives and the aldehydes or nitroso compounds is a dehydrating condensation reaction occurring at the methyl or methylene radical in the 2-position of the derivative. This reaction is described in detail in the afore-indicated U.S. patent which will be incorporated herein by reference.

Briefly, the starting indoline derivative and the aldehyde or nitroso compound may be heated to melt in the presence or absence of an organic or inorganic alkaline catalyst without use of any solvents or may be heated for reaction in non-polar, aprotic-type polar, or protonic-type solvents with or without use of an alkaline catalyst, thereby obtaining the derivatives of the general formula (II).

Alternatively, when the indoline derivatives and the aldehydes or nitroso compounds are reacted in organic acid anhydrides such as acetic anhydrice, propionic anhydride, etc. organic acids such as acetic acid, propionic acid, etc. and a mixture thereof, styryl dyes of the indolenium type alone are obtained (whose general formula will appear hereinlater as formula (IV)). In this case, the intended compounds of the general formula (II) may be obtained by treating the dyes with an alkaline agent or by dissolving once isolated dyes in suitable solvents such as methyl alcohol, ethyl alcohol and the like, and adding an alkaline agent to the solution with or without application of heat.

The alkaline agents or catalyts suitable for the purpose of the invention include organic ones such as, for example, triethylamine, piperidine, morpholine and the like and inorganic ones such as alkali carbonates, ammonia and the like.

After completion of the reaction, the reaction system is cooled to obtain crude crystals. If crude crystal can not be obtained by cooling, the solvent for the reaction is removed such as by distillation and then subjected to a treatment with water and, if necessary, may be heated or treated with active carbon in chloroform, acetone or ethyl ether, followed by removing the liquid. The resulting residue is crystallized by the use of a small amount of petroleum ether, n-hexane or the like and removed by filtration to obtain crude crystals.

The thus obtained crude crystals are then dissolved in chloroform, acetone, ethyl ether or the like and reprecipitated from petroleum ether, n-hexane, cyclohexane or the like. Alternatively, the solution of the crude crystals may be digested in n-hexane, cyclohexane, a mixture of ethyl ether and n-hexane or the like, followed by distilling off the solvent and then crystallizing from a solvent of the same type as used above. By the above procedure, the crude crystals are purified. The yield is in the range of about 55 to 81%.

The temperature and time required for the reaction between the indoline derivatives and the aldehyde or nitroso compounds are generally in ranges of about 50° to 100° C. and about 1 to 10 hours, respectively.

The starting aromatic or heterocyclic aldehydes and nitroso compounds usable in the present invention are those which are particularly described in the U.S. patent. That is, examples of the aromatic aldehydes include benzaldehyde, p-acetaminobenzaldehyde, p-bromobenzaldehyde, m-bromobenzaldehyde, o-bromobenzaldehyde, p-dimethylaminobenzaldehyde, p-diethylaminobenzaldehyde, p-dibutylaminobenzaldehyde, o-chlorobenzaldehyde, p-chlorobenzaldehyde, p-anisaldehyde, o-anisaldehyde, p-tolualdehyde, m-tolualdehyde, o-tolualdehyde, o-ethoxybenzaldehyde, p-ethoxybenzaldehyde, p-fluorobenzaldehyde, o-fluorobenzaldehyde, p-nitrobenzaldehyde, m-nitrobenzaldehyde, o-nitrobenzaldehyde, p-cyanobenzaldehyde, o-cyanobenzaldehyde, 2,4-dichlorobenzaldehyde, 2,6-dichlorobenzaldehyde, 3,4-dichlorobenzaldehyde, 3,5-dichlorobenzaldehyde, 2,4-dimethoybenzaldehyde, 2,5-dimethoxybenzaldehyde, 3,4-dimethoybenzaldehyde, 3,5-dimethoxybenzaldehyde, 2,4-dimethylbenzaldehyde, 2,5-dimethylbenzaldehyde, 3,4-dimethylbenzaldehyde, 3,5-dimethylbenzaldehyde, veratraldehyde (3,4-dimethoxybenzaldehyde), 4-isopropylbenzaldehyde, o-(2-chloroethyl)benzaldehyde, 2,4,6-trimethylbenzaldehyde(mesitylaldehyde), 2,4,6-triethoxybenzaldehyde, 3,4-dimethyl-p-anisaldehyde, 2,5-dimethyl-p-anisaldehyde, 2-chloro-5-nitrobenzaldehyde, 2-chloro-6-nitrobenzaldehyde, 2-chloro-3-nitrobenzaldehyde, 5-chloro-2-nitrobenzaldehyde, vanilin, o-vanilin, isovanilin, 5-bromo-vanilin, 2-chloro-4-dimethylaminobenzaldehyde, 2-chloro-6-fluorobenzaldehyde, 5-bromo-veratraldehyde, 6-bromo-veratraldehyde, 5-bromo-2-methoxybenzaldehyde, 1-naphthaladhyde, 2-naphthaladehyde, p-dimethylaminocinnamaldehyde, p-diethylcinnamaldehyde, p-nitrocinnamaldehyde, o-nitrocinnamaldehyde, 2-chlorocinnamaldehyde, 9-anthraldehyde, 10-chloro-9-anthraldehyde, 9-phenanthrenecarboaldehyde and fluorencarboxaldehyde.

Examples of the aromatic nitroso compounds include p-diemthylaminonitrosobenzene, p-diethylaminonitrosobenzene, p-methylnitroxobenzene (p-nitrosotoluene), p-nitronitrosobenzene, o-nitronitrosobenzene, 3-nitroso-2-nitrotoluene and the like.

Further, examples of the heterocyclic aldehydes include furfural, 5-methylfurfural, 5-bromofurfural, 4-isopropylfurfural, 2-thiophenecarboxaldehyde, 5-methylthiophenecarboxaldehyde, 9-methoxythiophene-2-carboxaldehyde, 2pyridinecarboxaldehyde, 3-pyridinecarboxaldehyde, 4-pyridinecarboxaldehyde, 1-ethylindole-3-carboxaldehyde, 1-methylindole-3-carboxaldehyde, 1-methyl-2-phenylindole-3-carboxaldehyde, N-methylcarbazole-2-carboxaldehyde, N-ethyl-7-bromocarbazole-2-carboxaldehyde, N-(n-octyl)-7-nitrocarbazole-2-carboxaldehyde, benzofuran-2-carboxaldehyde, dibenzofuran-2-carboxaldehyde, pyrrole-2aldehyde, N-methylpyrrole-2-aldehyde, N-phenylpyrrole-2-aldehyde, 3-methylpyrrole-2-aldehyde, 2-ethylpyrrole-5-aldehyde, benzothiazole-2-aldehyde, 6-methylbenzothiazole-2-aldehyde, 6-chlorobenzothiazole-2-aldehyde, 5-chlorobenzothiazole-2-aldehyde, 6-methoxybenzothiazole-2-aldehyde, 5,6-dichlorobenzothiazole-2-aldehyde, benzoselenazole-2-aldehyde, 6-methoxybenzoselenazole-2-aldehyde, 2,4-dimethylpyrrole-2-aldehyde, 4,6-dichloropyrimidine-5-carboxaldehyde, 2-formyl-4,6-dimethylpyrimidine, quinoline-2-aldehyde, acridine-10aldehyde, 2,4-diphenyl-5,6,7-hexahydrobenzopyran-8-carboxaldehyde, 2,4-diphenyl-6-methyl-5,6,7-pentahydrobenzopyran-8-carboxaldehyde and the like.

Examples of the heterocyclic nitroso compounds include 3-nitrosoindole, 2-methyl-3-nitrosoindole (3-nitrosomethylketol), 3-nitroso-2-phenylindole and the like.

The new derivatives of the styryl-like compounds according to the invention are characterized by their substituents attached to the benzene ring of the indoline derivative. Although it is stated in the prior U.S. patent that Q of the styryl-like compound of the general formula (I) represents a benzene ring with or without substituted radicals, such a radical is a halogen, a nitro group, methyl, methoxy or phenyl, not including radicals containing sulfur and two or more oxygen atom, e.g. sulfonyl groups.

The derivatives of the styryl-like compounds according to the invention have several advantages that incorporation of $RO_nS$—radical ensures a remarkable improvement in lifetime and stability of the derivatives when they are subjected to a repeated cycle of coloration and bleaching or color change, that almost all of the derivatives except some compounds have absorptions in the ultraviolet ray regions and are originally colorless to light yellow in color, and that highly pure derivatives of the general formula (II) can be obtained more easily because the $RO_nS$—group is introduced into the indoline derivatives so that they are readily crystallized. With known styryl-like compounds free of the $OR_nS$ group, some compounds become poor in crystallinity, needing additional steps of purifying the compounds.

When applied with an external activating energy such as light, heat, ions, electric potential, pressure, radiant ray or the like, the derivatives of the styrl-like compounds of the general formula (II) are converted into a ring-opened, colored state of the indolenium structure represented by the general formula (IV)

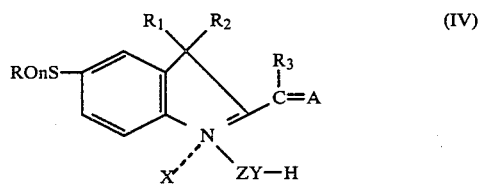

in which R, $R_1$, $R_2$, $R_3$, A, Y and Z have the same meanings as defined in the formula (II) and X represents an anion such as halogen, acid radical or alkoxy anion, thereby showing color in the near-ultraviolet and near-infrared spectrum regions and in the whole region of visible light.

The ring-opened, colored structure of the indolenium type may be returned to the original ring-closed, bleached or colorless structure of the indoline type when an external activating energy is applied in the opposite direction or is removed.

The interchange of the chemical structures between the general formulas (II) and (IV) caused by the external energy results in a reversible change from coloration to bleaching or vice versa. In this connection, however, when styryl-like compounds which are free of $RO_nS$—group are subjected to the repeated cycle of coloration and bleaching, they naturally suffer deterioration in properties an frequently involve coloration even after an external energy has been removed. It has been found that such deterioration can be overcome to a fair extent by incorporation of the $RO_nS$ group into the styryl-like compounds. That is, the lifetime can be prolonged to ten or more times as long as that of the $RO_nS$ group-free styryl-like compounds.

Then, synthetic examples of the derivatives of the general formula (II) are described by way of illustration only.

Synthetic Example 1

1.13 g of 2,3,3-trimethyl-5-methylsulfonyl-indolino[2.1-b]oxazoline and 0.6 g of para-dimethylaminobenzaldehyde were dissolved in water-free benzene, to which was added 0.22 ml of triethylamine, followed by refluxing for 4 hours under heating conditions. Then, the solvent was removed by distillation and the residue was crystallized from petroleum ether. After cooling, the crystals were separated from the reaction system by suction filtration. The resulting crude crystals were dissolved in 30 ml of acetone under heating conditions, treated with active carbon, filtered and washed with acetone. The filtrate and washing were combined and concentrated to 6-7 ml and cooled, followed by diluting with cold water to obtain crystals. The crystals were suction filtered and dried in a desiccator to give 1.55 g of crystals which were creamy in color.

The crystals were subsequently dissolved in 30 ml of acetone and filtered. The filtrate was placed on a water bath of 65° C. to remove the acetone for concentration to 6-7 ml, followed by recrystallization from a mixture of ethyl ether and petroleum ether, filtering and washing with an ethyl ether/petroleum ether mixture, and drying in a desiccator to obtain 1.32 g of creamy, purified crystals (yield 80%).

The purified crystals were confirmed by elementary and NMR analyses to be 3,3-dimethyl-5-methylsulfonyl-2-(p-dimethylaminostyryl)-indolino[2.1-b]oxazoline of the following formula (1) with a molecular weight of 412.

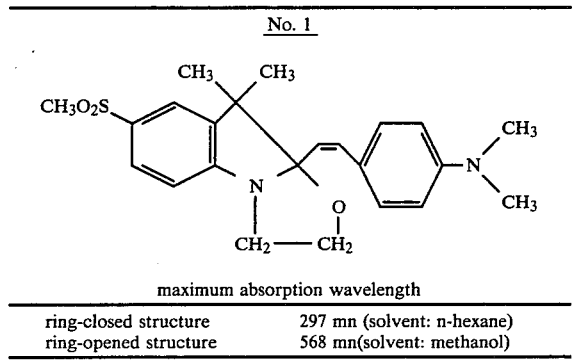

| | No. 1 |
|---|---|
| | maximum absorption wavelength |
| ring-closed structure | 297 mn (solvent: n-hexane) |
| ring-opened structure | 568 mn (solvent: methanol) |

Synthetic Examples 2-29

Synthetic example 1 was repeated using starting materials and reaction condition indicated in Table shown below.

TABLE

| Ex. No. | Starting Materials (amounts) | | Reaction Temp. (°C.) | Reaction Time (hrs) | Catalyst | Solvent | Yield (g) |
|---|---|---|---|---|---|---|---|
| | Indoline Derivative | Aromatic or Heterocyclic Aldehyde or Nitroso Compound | | | | | |
| 2 | 2,3,3-trimethyl-5-methylsulfonyl-2-(3,4-dioxymethylenestyryl)-indolino[2.1-b]oxazoline (1.41 g) | piperonal (0.75 g) | 90-95 | 6 | triethylamine | dioxane | 1.05 |
| 3 | 2,3,3-trimethyl-5-methylsulfonyl-2-(3,4-dioxymethylenestyryl)- | p-dimethylaminobenzaldehyde | 90-95 | 6 | triethylamine | mixed solvent of actone | 1.18 |

TABLE-continued

| Ex. No. | Starting Materials (amounts) Indoline Derivative | Aromatic or Heterocyclic Aldehyde or Nitroso Compound | Reaction Temp. (°C.) | Reaction Time (hrs) | Catalyst | Solvent | Yield (g) |
|---|---|---|---|---|---|---|---|
|  | indolino[2.1-b]oxazoline (1.18 g) | (0.6 g) |  |  |  | and ethanol |  |
| 4 | 2,3,3-trimethyl-5-methylsulfonyl-2-(3,4-dioxymethylenestyryl)-indolino[2.1-b]oxazoline (1.55 g) | p-anisaldehyde (0.82 g) | 100 | 4 | morpholine | nil | 1.01 |
| 5 | 2,3,3-trimethyl-5-methylsulfonyl-2-(3,4-dioxymethylenestyryl)-indolino[2.1-b]oxazoline (1.13 g) | p-dimethylamino-cinnamaladhyde (0.7 g) | 85 | 2.5 | triethylamine | mixed solvent of chloroform and acetone | 1.05 |
| 6 | 2,3,3-trimethyl-5-methylsulfonyl-2-(3,4-dioxymethylenestyryl)-indolino[2.1-b]oxazoline (1.13 g) | 9-methyl-carbazole-3-carboxaldehyde (0.84 g) | 60 | 3 | piperidine | mixed solvent of benzene and methyl ethyl ketone | 1.17 |
| 7 | 2,3,3-trimethyl-5-methylsulfonyl-2-(3,4-dioxymethylenestyryl)-indolino[2.1-b]oxazoline (1.41 g) | 9-n-octyl-carbazole-3-carboxaldehyde (1.54 g) | 100 | 3.5 | triethylamine | dimethylformamide | 1.08 |
| 8 | 2,3,3-trimethyl-5-(n-butylsulfonyl)indolino[2.1-b]oxazoline (1.62 g) | p-dimethylamino-benzaldehyde (0.75 g) | 90 | 4 | nil | ethanol (fractionation with ethyl ether and n-hexane) | 1.21 |
| 9 | 2,3,3-trimethyl-5-(n-butylsulfonyl)indolino[2.1-b]oxazoline (1.62 g) | p-acetylamino-benzaldehyde (0.82 g) | 60–65 | 7 | nil | n-hexane | 1.25 |
| 10 | 2,3,3-trimethyl-5-(n-butylsulfonyl)indolino[2.1-b]oxazoline (1.78 g) | 1-methyl-2-(p-nitrophenyl)-indole-3-carboxaldehyde (1.46 g) | 90–95 | 5 | triethylamine | ethyl acetate | 1.36 |
| 11* | 2,3,3-trimethyl-5-(n-octylsulfonyl)-indolino[2.1-b]oxazoline (1.77 g) | p-dimethylaminobenzaldehyde (0.67 g) | 100 | 4 | nil | acetic anhydride | 1.35 |
| 12 | 2,3,3-trimethyl-5-(n-octylsulfonyl)-indolino[2.1-b]oxazoline (1.77 g) | p-tolylaldehyde (0.6 g) | 85 | 5.5 | triethylamine | acetone | 0.97 |
| 13 | 2,3,3-trimethyl-5-phenylsulfonyl-indolino[2.1-b]oxazoline (1.71 g) | p-dimethylamino-benzaldehyde (0.75 g) | 90–95 | 5 | piperidine | benzene | 1.3 (55%) |
| 14 | 2,3,3-trimethyl-5-phenylsulfonyl-indolino[2.1-b]oxazoline (1.71 g) | p-bromobenzaldehyde (1.0 g) | 90–95 | 6 | triethylamine | mixed solvent of benzene and ethyl acetate | 1.12 (44%) |
| 15 | 2,3,3-trimethyl-5-phenylsulfonyl-indolino[2.1-b]oxazoline (1.71 g) | p-amisaldehyde (0.7 g) | 80–85 | 5 | triethylamine | acetone | 1.22 (53%) |
| 16 | 2,3,3-trimethyl-5-phenylsulfonyl-indolino[2.1-b]oxazoline (1.37 g) | 1-ethyl-indole-3-carboxaldehyde (0.70 g) | 90 | 3.5 | triethylamine | mixed solvent or benzene and acetone | 1.34 (67%) |
| 17 | 2,3,3-trimethyl-5-phenylsulfonyl-indolino[2.1-b]oxazoline (1.54 g) | 9-n-butyl-3-carbazole-carboxaldehyde (1.12 g) | 90 | 3 | triethylamine | dioxane | 1.67 (65%) |
| 18 | 2,3,3-trimethyl-5-methylsulfonyl-indolino[2.1-b]oxazoline (1.41 g) | p-chlorobenzaldehyde (0.63 g) | 90 | 4 | triethylamine | benzene | 1.13 (46%) |
| 19 | 2,3,3-trimethyl-5-methylsulfonyl-indolino[2.1-b]oxazoline (1.13 g) | p-di-n-butylaminobenzaldehyde (0.94 g) | 90 | 3.5 | triethylamine | tetrahydrofuran | 1.48 (75%) |
| 20 | 2,3,3-trimethyl-5-n-butylsulfonyl-indolino[2.1-b]tetrahydro-1,3-oxazine (1.35 g) | p-diethylaminobenzaldehyde (0.72 g) | 90 | 3 | morpholine | benzene | 1.36 (69%) |
| 21 | 2,3,3-trimethyl-5-methylsulfonyl-2-(p-dimethylamino-2-azastyryl)-indolino[2.1-b]oxazoline (1.41 g) | p-dimethylamino-nitrobenzene (0.77 g) | 90 | 4 | nil | mixed solvent of ethanol and benzene | 1.26 (61%) |
| 22 | 2,3,3-trimethyl-5-methylsulfonyl-indolino[2.1-b]thiazoline (1.41 g) | p-dimethylamino-benzaldehyde (0.61 g) | 90 | 3 | triethylamine | mixed solvent of benzene and acetone | 1.34 |
| 23 | 2,3,3-trimethyl-5-phenylsulfonyl-indolino[2.1-b]thiazole (1.37 g) | p-dimethylamino-benzaldehyde (0.62 g) | 90 | 3.5 | triethylamine | tetrahydrofuran | 1.37 |
| 24 | 2,3,3-trimethyl-5-methysulfonyl-indolino[2.1-b]oxazoline (1.41 g) | 3,4-dimethoxybenzaldehyde (0.85 g) | 90 | 5 | triethylamine | benzene | 1.02 |
| 25 | 3,3-dimethyl-2-ethyl-5-methylsulfonyl-indolino[2.1-b]oxazoline | p-dimethylaminobenzaldehyde | 85–90 | 4 | triethylamine | acetonitrile | 0.98 (58%) |

TABLE-continued

| Ex. No. | Starting Materials (amounts) Indoline Derivative | Aromatic or Heterocyclic Aldehyde or Nitroso Compound | Reaction Temp. (°C.) | Reaction Time (hrs) | Catalyst | Solvent | Yield (g) |
|---|---|---|---|---|---|---|---|
| 26 | (1.2 g) 2,3,3-trimethyl-5-methylsulfonyl-indolino[2.1-b]-5-methyloxazoline (1.18 g) | (0.6 g) p-dimethylaminobenzaldehyde (0.62 g) | 90 | 3.5 | triethylamine | mixed solvent of acetonitrile and dioxane | 1.28 |
| 27 | 2,3-dimethyl-3-ethoxymethyl-5-methylsulfonyl-indolino[2.1-b]-oxazoline (1.20 g) | p-dimethylaminobenzaldehyde (0.65 g) | 90 | 4 | triethylamine | mixed solvent of acetonitrile and dichloroethane | 1.21 |
| 28 | 2,3,3-dimethyl-5-(n-butoxysulfonyl)-2-(p-dimethylaminostyryl)-indolino[2.1-b]-oxazoline (1.34 g) | p-dimethylaminobenzaldehyde (0.70 g) | 90 | 4 | piperidine | mixed solvent of acetonitrile and dioxane | 1.25 |
| 29 | 2,3,3-trimethyl-5-(n-butoxysulfonyl)-indolino[2.1-b]-oxazoline (1.49 g) | p-anisbenzaldehyde (0.71 g) | 85-90 | 5.5 | triethylamine | mixed solvent of benzene and ethanol | 1.17 |

*Note: Crude crystals of the indolenium dye were treated with methanol/ammoniacal solution to obtain an intended compound.

A a result, there were obtained compound No. 2-29 of the structural formulas shown below together with their maximum absorption wavelengths in ring-closed and ring-operated states.

No. 2 3,3-dimethyl-5-methylsulfonyl-2-(3,4-dioxymethylenestyryl)-indolino[2.1-b]oxazoline

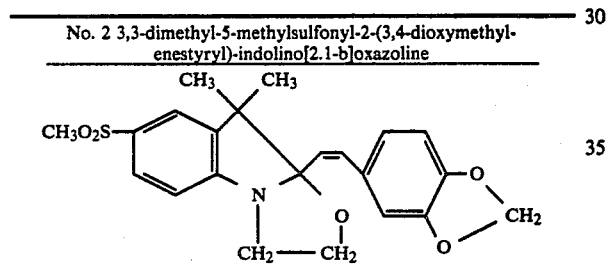

maximum absorption wavelength

| ring-closed structure | 266 nm (solvent: n-hexane) |
|---|---|
| ring-opened structure | 465 nm (solvent: methanol) |

No. 3 3,3-dimethyl-5-methylsulfonyl-2-(p-dimethylaminostyryl)indolino[2.1-b]tetrahydro-1,3-oxazine

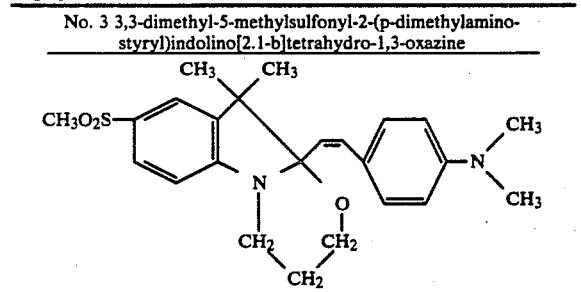

maximum absorption wavelength

| ring-closed structure | 299 nm (solvent: n-hexane) |
|---|---|
| ring-opened structure | 569 nm (solvent: methanol) |

No. 4 3,3-dimethyl-5-methylsulfonyl-2-(p-methoxystyryl)-indolino[2.1-b]oxazoline

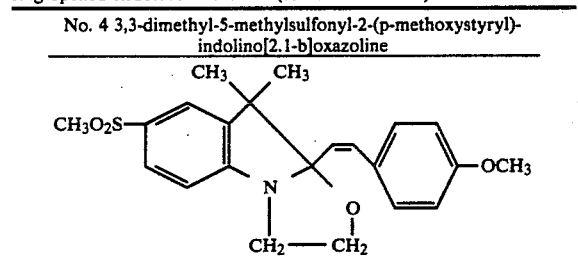

maximum absorption wavelength

| ring-closed structure | 274 nm (solvent: n-hexane) |
|---|---|
| ring-opened structure | 450 nm (solvent: methanol) |

No. 5 3,3-dimethyl-5-methylsulfonyl-2-{4-(p-dimethylaminophenyl)-1,3-butadienylene}indolino[2.1-b]oxazoline

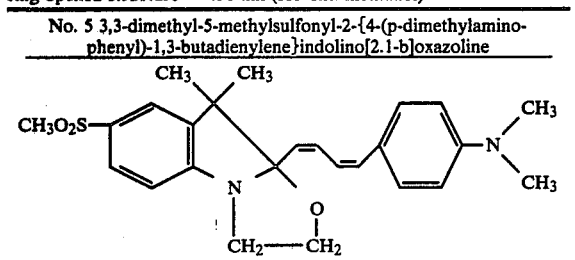

maximum absorption wavelength

| ring-closed structure | 334 ~336 nm (solvent: n-hexane) |
|---|---|
| ring-opened structure | 648 nm (solvent: methanol) |

No. 6 3,3-dimethyl-5-methylsulfonyl-2-{2-(9-methyl-3-carbazolyl)vinylene}indolino[2.1-b]oxazoline

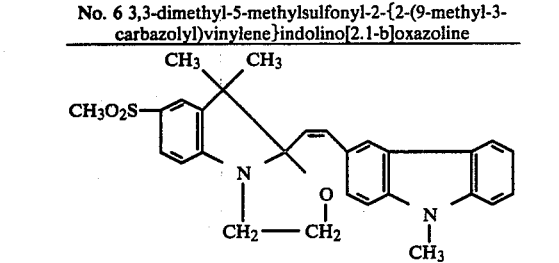

maximum absorption wavelength

| ring-closed structure | 285 nm (solvent: n-hexane) |
|---|---|
| ring-opened structure | 526 nm (solvent: methanol-acetic acid) |

No. 7 3,3-dimethyl-5-methylsulfonyl-2-{2-(9-n-octyl-3-carbazolyl)vinylene}indolino[2.1-b]oxazoline

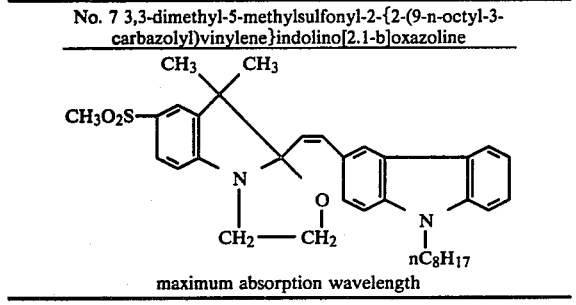

maximum absorption wavelength

-continued

| ring-closed structure | 286.5 nm (solvent: n-hexane) |
|---|---|
| ring-opened structure | 528 nm (solvent: methanol-acetic acid) |

No. 8 3,3-dimethyl-5-(n-butylsulfonyl)-2-(p-dimethylamino-styryl)indolino[2.1-b]oxazoline

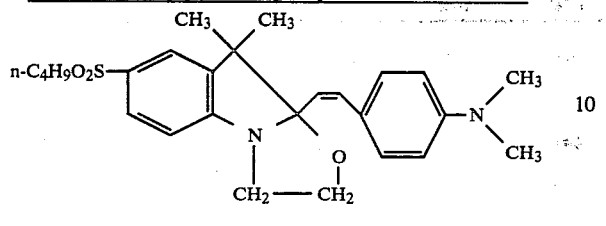

maximum absorption wavelength

| ring-closed structure | 300 nm (solvent: n-hexane) |
|---|---|
| ring-opened structure | 571 nm (solvent: methanol) |

No. 9 3,3-dimethyl-5-(n-butylsulfonyl)-2-(p-acetylamino-styryl)indolino[2.1-b]oxazoline

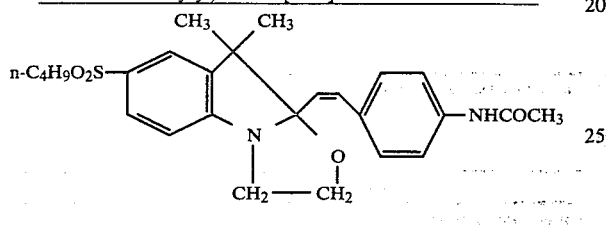

maximum absorption wavelength

| ring-closed structure | 286 nm (solvent: n-hexane) |
|---|---|
| ring-opened structure | 552 nm (solvent: methanol) |

No. 10 3,3-dimethyl-5-(n-butylsulfonyl)2-{2-[1-methyl-2-(p-nitrophenyl)-3-indolyl]vinyl}indolino[2.1-b]-oxazoline

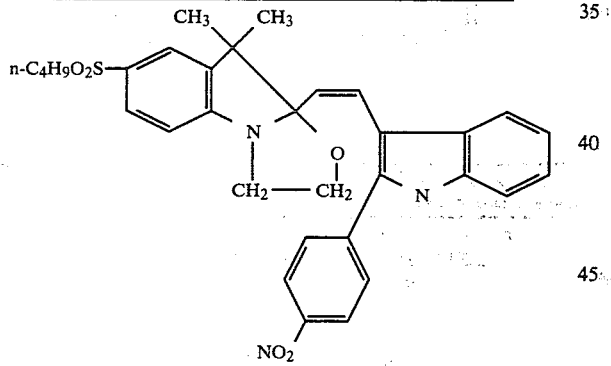

maximum absorption wavelength

| ring-closed structure | 245 nm. 262 nm (solvent: n-hexane) |
|---|---|
| ring-opened structure | 515 nm (solvent: methanol-acetic acid) |

No. 11 3,3-dimethyl-5-(n-octylsulfonyl)-2-(p-dimethylamino-styryl)indolino[2.1-b]oxazoline

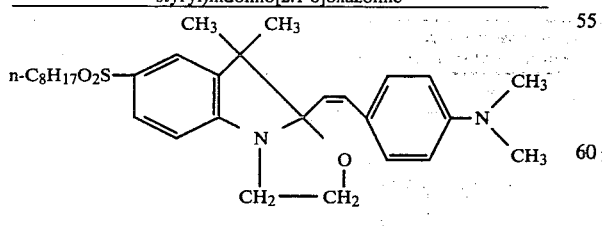

maximum absorption wavelength

| ring-closed structure | 300 nm (solvent: n-hexane) |
|---|---|
| ring-opened structure | 572 nm (solvent: methanol) |

No. 12 3,3-dinmethyl-5-(n-octylsulfonyl)-2-(p-methylstyryl)-indolino[2.1-b]oxazoline

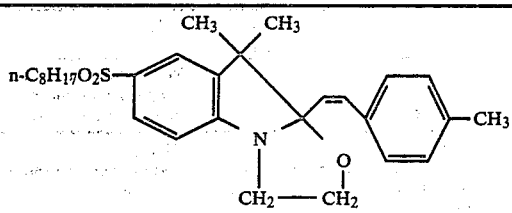

maximum absorption wavelength

| ring-closed structure | 255~257 nm (solvent: n-hexane) |
|---|---|
| ring-opened structure | 417~418 nm (solvent: methanol) |

No. 13 3,3-dimethyl-5-phenylsulfonyl-2-(p-dimethylamino-styryl)indolino[2.1-b]oxazoline

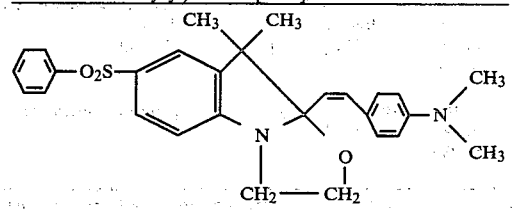

maximum absorption wavelength

| ring-closed structure | 300 nm (solvent: n-hexane) |
|---|---|
| ring-opened structure | 574 (solvent: methanol) |

No. 14 3,3-dimethyl-5-phenylsulfonyl-2-(p-bromostyryl)-indolino[2.1-b]oxazoline

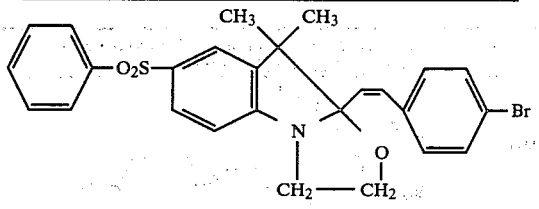

maximum absorption wavelength

| ring-closed structure | 270~272 nm (solvent: n-hexane) |
|---|---|
| ring-opened structure | 405~406 nm (solvent: methanol) |

No. 15 3,3-dimethyl-5-phenylsulfonyl-2-(p-methoxystyryl)-indolino[2.1-b]oxazoline

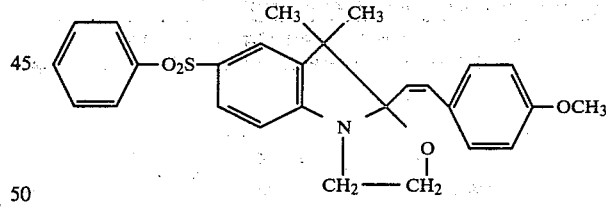

maximum absorption wavelength

| ring-closed structure | 276~277 nm (solvent: n-hexane) |
|---|---|
| ring-opened structure | 452 nm (solvent: methanol) |

No. 16 3,3-dimethyl-5-phenylsulfonyl-2-{2-(1-ethyl-3-indolyl)vinyl}indolino[2.1-b]oxazoline

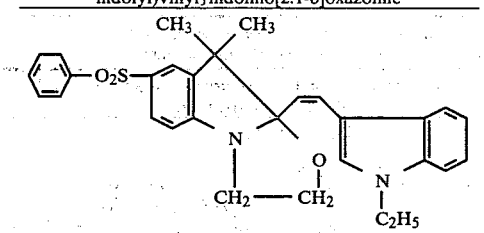

maximum absorption wavelength

| ring-closed structure | 292 nm. 267 nm (solvent: n-hexane) |
|---|---|
| ring-opened structure | 505 nm (solvent: methanol) |

No. 17 3,3-dimethyl-5-phenylsulfonyl-2-{2-(9-n-butyl-3-carbazolyl)vinylene}indolino[2.1-b]oxazoline

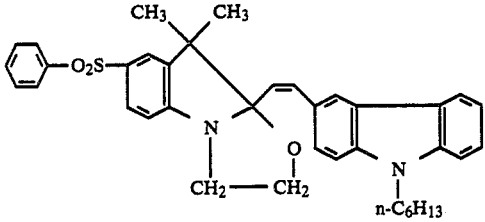

maximum absorption wavelength

| | |
|---|---|
| ring-closed structure | 287 nm (solvent: n-hexane) |
| ring-opened structure | 529 nm (solvent: methanol-acetic acid) |

No. 18 3,3-dimethyl-5-methylsulfonyl-2-(p-chlorostyryl)-indolino[2.1-b]oxazoline

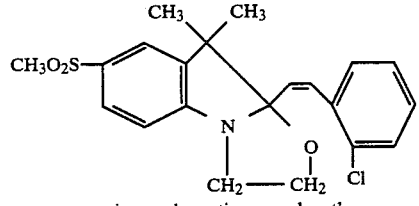

maximum absorption wavelength

| | |
|---|---|
| ring-closed structure | 247 nm (solvent: n-hexane) |
| ring-opened structure | 414 nm (solvent: methanol) |

No. 19 3,3-dimethyl-5-methylsulfonyl-2-(p-di-n-butylaminostyryl)indolino[2.1-b]oxazoline

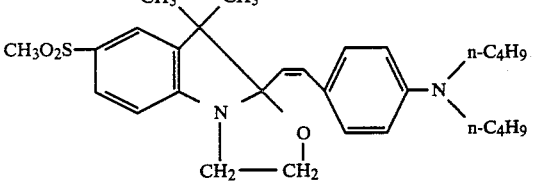

maximum absorption wavelength

| | |
|---|---|
| ring-closed structure | 301~303 nm (solvent: n-hexane) |
| ring-opened structure | 570 nm (solvent: methanol) |

No. 20 3,3-dimethyl-5-n-butylstyryl-2-(p-diethylaminostyryl)-indolino[2.1-b]oxazoline

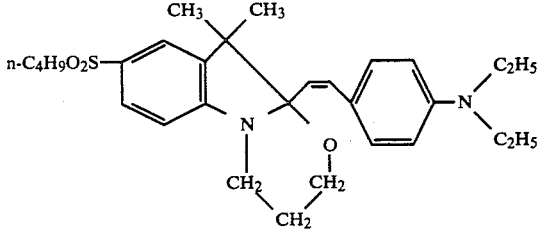

maximum absorption wavelength

| | |
|---|---|
| ring-closed structure | 301 nm (solvent: n-hexane) |
| ring-opened structure | 569 nm (solvent: methanol) |

No. 21 3,3-dimethyl-5-methylsulfonyl-2-(p-dimethylamino-2-azastyryl)indolino[2.1-b]oxazoline

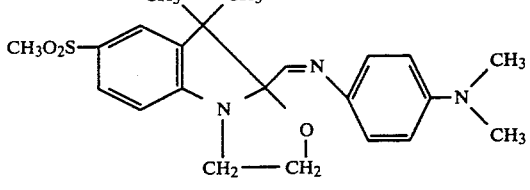

maximum absorption wavelength

| | |
|---|---|
| ring-closed structure | 293 nm (solvent: n-hexane) |
| ring-opened structure | 612–614 nm (solvent: methanol) |

No. 22 3,3-dimethyl-5-methylsulfonyl-2-(p-dimethylamino)-indolino[2.1-b]thiazole

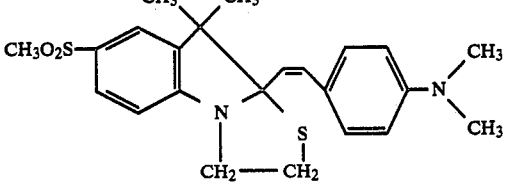

maximum absorption wavelength

| | |
|---|---|
| ring-closed structure | 402~403 nm (solvent: dimethylcarbonate) |
| ring-opened structure | 544~546 nm (solvent: dimethyl carbonate) |

No. 23 3,3-dimethyl-5-phenylsulfonyl-2-(p-dimethylaminostyryl)indolino[2.1-b]thiazoline

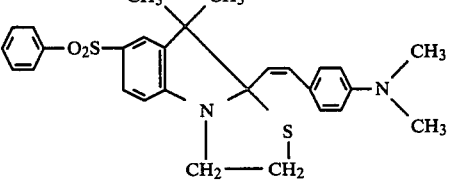

maximum absorption wavelength

| | |
|---|---|
| ring-closed structure | 403 nm (solvent: n-hexane) |
| ring-opened structure | 549~550 nm (solvent: dimethyl carbonate) |

No. 24 3,3-dimethyl-5-methylsulfonyl-2-(3,4-dimethoxystyryl)indolino[2.1-b]oxazoline

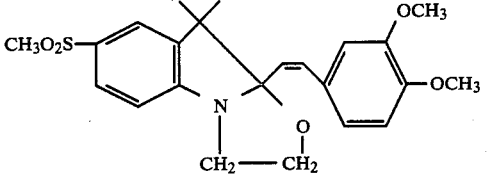

maximum absorption wavelength

| | |
|---|---|
| ring-closed structure | 266–268 nm (solvent: n-hexane) |
| ring-opened structure | 459 nm (solvent: methanol) |

No. 25 3,3-dimethyl-5-methylsulfonyl-2-{1-methyl-2-(p-dimethylaminostyryl)}indolino[2.1-b]oxazoline

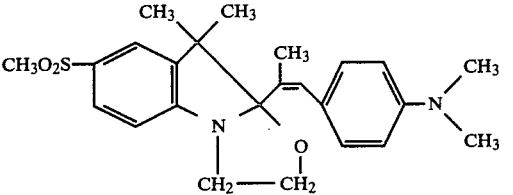

maximum absorption wavelength

| | |
|---|---|
| ring-closed structure | 292~293 nm (solvent: n-hexane) |
| ring-opened structure | 565~567 nm (solvent: methanol) |

No. 26 3,3-dimethyl-5-methylsulfonyl-2-(p-dimethylaminostyryl)indolino[2.1-b]-5-methyloxazoline

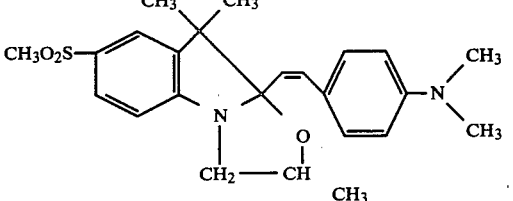

-continued maximum absorption wavelength

| | |
|---|---|
| ring-closed structure | 299~300 nm (solvent: n-hexane) |
| ring-opened structure | 567 nm (solvent: dimethyl carbonate-methanol) |

No. 27 3-methyl-3-ethoxymethyl-5-methylsulfonyl-2-(p-dimethyl-aminostyryl)indolino[2.1-b]oxazoline maximum absorption wavelength

| | |
|---|---|
| ring-closed structure | 294~6 nm (solvent: n-hexane) |
| ring-opened structure | 565~567 nm (solvent: dimethyl carbonate methanol) |

No. 28 3,3-dimethyl-5-(n-butoxysulfonyl)-2-(p-dimethyl-aminostyryl)indolino[2.1-b]oxazoline maximum absorption wavelength

| | |
|---|---|
| ring-closed structure | 294~295 nm (solvent: n-hexane) |
| ring-opened structure | 560 nm (solvent: dimethyl carbonate-methanol) |

No. 29 3,3-dimethyl-5-(n-butoxysulfonyl)-2-(p-methoxystyryl)-indolino[2.1-b]oxazoline maximum absorption wavelength

| | |
|---|---|
| ring-closed structure | 269~270 nm (solvent: n-hexane-petroleum benzine) |
| ring-opened structure | 444~445 nm (solvent: methanol) |

The derivatives according to the invention are practically applied in various manners. That is, the derivatives are dissolved in organic solvents including, for example, hydrocarbons such as n-hexane, sulfoxides such as dimethyl sulfoxide, lactones, nitriles such as acetonitrile, carbonates such as propylene carbonate, amides such as dimethylformamide and the like.

The solution may be applied onto a paper sheet or the like and dried, to which an ultraviolet ray is applied to develop color. Alternatively, when the solution is placed between two glass plates which have been sealed and heat is applied, coloration takes place. Still alternatively, the solution may be placed in a glass cell with transparent electrodes. When an electric potential is applied between the electrodes, the derivative dissolved in the solution is converted into a corresponding indolenium structure, and thus shows color.

Further, the coloration of the derivatives may be fixed, if desired. These applications will be particularly described in Examples which follow.

EXAMPLE 1

3,3-dimethyl-5-methylsulfonyl-2-(p-dimethylaminostyryl)indolino[2.1-b]oxazoline of the structural formula (1) was dissolved in n-hexane and the solution was applied onto a paper sheet, followed by removing the solvent by evaporation. When exposed to an ultraviolet ray, the thus applied sheet showed a purple color. The colored state was held over a relatively long time after elimination of the exposure. Presumably, this is because the compound of the chemical structure (1) is excited by exposure to ultraviolet ray and is ring-opened by means of anions contained in the paper sheet and protons water thereby developing the color. When the styryl-like compound to the invention and a known styryl-like compound (where no methylsulfonyl group is contained) were subjected to a continuous irradiation of ultraviolet ray for comparison in stability, it was found that the known styryl-like compound began to fade about 1 hour after the irradiation but the compound according to the invention showed no fading or bleaching up to about 10 hours.

EXAMPLE 2

3,3-dimethyl-5-(n-butylsulfonyl)-2-p-dimethylaminostyryl)indolino[2.1-b]oxazoline of the formula (8) was dissolved in dimethyl sulfoxide and the solution was placed between two glass plates. On application of heat, it was found that the oxazoline compound changed in color from colorless to reddish purple when the temperature reached about 125° C. The color development by application of heat occured in the vicinity of a melting point of the styryl-like compound and when protons or anions were present, it showed a color at temperatures much lower than the melting point.

Other styryl-like compounds according to the invention developed inherent colors, respectively, by application of heat thereto. For instance, when 3,3-dimethyl-5-methylsulfonyl-2-(3,4-methylenedioxystyryl)indolino[2.1-b]oxazoline of the formula (2) alone was heated, the oxazoline compound changed from colorless to yellowish orange in color at about 177° C. Further, when dissolved in dimethyl sulfoxide admixed with a small amount of methyl alcohol and heated, the oxazoline compound showed a yellowish orange color at about 50° C. As is noted from the above, an increase in concentration of protons results in a color development at lower temperature.

EXAMPLE 3

3,3-dimethyl-5-phenylsulfonyl-2-(p-dimethylaminostyryl)indolino[2.1-b]oxazoline of the structural formula (13) and tetrabutyl ammonium perchlorate were dissolved in γ-butyrolactone each in an amount of 0.1 mole/l.

Then, the solution was sealed in a glass cell having transparent electrodes as shown in the sole FIGURE. In the FIGURE, there is shown a glass cell 10 having glass plates 11, 12 attached with transparent conductive films 13, 14 made of indium oxide, respectively. Indicated at 15 is a spacer made of an epoxy resin and serving also to seal the solution between the glass plates, and at 16 is the above-mentioned solution dissolving the styryl-like compound therein.

When a d.c. voltage of 1.0–1.5 V was applied between the conductive films or electrodes, the solution 16 showed a purple color. The application of the d.c. voltage was stopped, whereupon the solution was returned to an original colorless state. Especially when a d.c. voltage of the polarity opposite to that used at the color development was applied, the bleaching speed was accelerated.

On comparison with a known styryl-like compound which was free of the phenylsulfonyl group, the modified styryl-like compound according to the invention was found to show a lifetime ten times as long as the known compound when repeating the coloration and bleaching cycle.

Similar results were obtained using other modified styryl-like compounds according to the invention.

In the above procedure, γ-butyrolactone was used as a solvent. In practice, aprotic solvents such as acetonitrile, propylene carbonate, dimethylformamide and the like are suitably usable instead. Moreover, instead of tetraethyl ammonium perchlorate there are usable lithium perchlorate, tetramethyl ammonium hexafluorophosphate and the like as a supporting salt. Dissociated ions of the supporting salt take part in the coloration and bleaching mechanism which is caused by oxidation and reduction thereof with electrodes.

EXAMPLE 4

3,3-dimethyl-5-(n-butylsulfonylstyryl)indolino[2.1-b]oxazoline of the structural formula (9) and terra abla were dispersed in gelatin so that they were not contacted each other and the dispersion was applied onto a paper sheet thinly. By application of pressure, the oxazoline dye was contacted with the terra abla in regions where pressure was applied to develop a red color. In this case, the developed color was fixed. When a known styryl-like compound was used, it was found difficult to keep the dispersion in a non-colored state because of its poor stability.

With the styryl-like compounds of the invention, little troubles were involved in coloration when dispersed together with terra abla.

EXAMPLE 5

3,3-ddimethyl-5-methylsulfonyl-2-(p-dimethylaminocinnamylidenevinyl)indolino[2.1-b]oxazoline of the structural formula (5) and hydroquinone were dispersed in gelatin each in an amount of about 0.01 mole and the dispersion was applied onto a paper sheet thinly. When exposed to a radiant ray such as an electron ray, α-ray, β-ray or the like, the applied layer was colored in indigo blue. The coloration was held for a time after the irradiation of the radiant ray had been stopped and then the layer was gradually returned to a bleached state. As compared with known styryl-like compounds, the modified styryl-like compounds of the invention are advantageous in that a time before the bleaching begins is longer by one order of magnitude than that necessary for the known compounds.

EXAMPLE 6

Example 5 was repeated using 3,3-dimethyl-5-phenylsulfonyl-2-{3-(1-ethylinodolyl)vinyl}indolino[2.1-b]oxazoline of the structural formula (8) instead of the styryl-like compound of the structural formula (5). On exposure to a radiant ray, a clear red color was developed and retained for a while. The retaining time was longer than in case where a known oxazoline compound free of the phenylsulfonyl group was used.

What is claimed is:

1. A styryl-like compound showing a color-developing and bleaching behavior with improved stability and prolonged lifetime and represented by the general formula

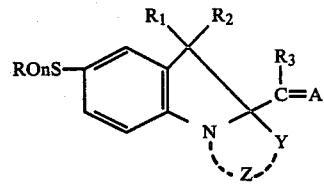

in which R represents an alkyl or phenyl group, $R_1$ and $R_2$ independently represent a lower alkyl group, a hydroxyalkyl group, or an alkoxyalkyl group, $R_3$ represents hydrogen, an alkyl group, a halogen, a nitrile group, an aromatic group or a phenoxy group, Y represents O or S, Z represents an alkylene radical or 2 to 4 carbon atoms, with or without alkyl substituent(s), necessary for forming a ring structure together with

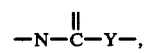

A represents a residue of an aromatic aldehyde, selected from the group consisting of benzaldehyde, p-acetaminobenzaldehyde, p-bromobenzaldehyde, m-bromobenzaldehyde, o-bromobenzaldehyde, p-dimethylaminobenzaldehyde, p-diethylaminobenzaldehyde, p-dibutylaminobenzaldehyde, o-chlorobenzaldehyde, p-chlorobenzaldehyde, p-anisaldehyde, o-anisaldehyde, p-tolualdehyde, m-tolualdehyde, o-tolualdehyde, o-ethoxybenzaldehyde, p-ethoxybenzaldehyde, p-fluorobenzaldehyde, o-fluorobenzaldehyde, p-nitrobenzaldehyde, m-nitrobenzaldehyde, o-nitrobenzaldehyde, p-cyanobenzaldehyde, o-cyanobenzaldehyde, 2,4-dichlorobenzaldehyde, 2,6-dichlorobenzaldehyde, 3,4-dichlorobenzaldehyde, 3,5-dichlorobenzaldehyde, 2,4-dimethoxybenzaldehyde, 2,5-dimethoxybenzaldehyde, 3,4-dimethoxybenzaldehyde, 3,5-dimethoxybenzaldehyde, 2,4-dimethylbenzaldehyde, 2,5-dimethylbenzaldehyde, 3,4-dimethylbenzaldehyde, 3,5-dimethylbenzaldehyde, veratraldehyde(3,4-dimethoxybenzaldehyde), 4-isopropylbenzaldehyde, o-(2-chloroethyl)benzaldehyde, 2,4,6-trimethylbenzaldehyde(mesitylaldehyde), 2,4,6-triethoxybenzaldehyde, 3,4-dimethyl-p-anisaldehyde, 2,5-dimethyl-p-anisaldehyde, 2-chloro-5-nitrobenzaldehyde, 2-chloro-6-nitrobenzaldehyde, 2-chloro-3-nitrobenzaldehyde, 5-chloro-2-nitrobenzaldehyde, vanilin, o-vanilin, iso-vanilin, 5-bromo-vanilin, 2-chloro-4-dimethylaminobenzaldehyde, 2-chloro-6-fluorobenzaldehyde, 5-bromo-veratraldehyde, 6-bromo-veratraldehyde, 5-bromo-2-methoxybenzaldehyde, 1-naphthaladhyde, 2-naphthaladehyde, p-dimethylaminocinnamaldehyde, p-diethylcinnamaldehyde, p-nitrocinnamaldehyde, o-nitrocinnamaldehyde, 2-chlorocinnamaldehyde, 9-anthraldehyde, 10-chloro-9-anthraldehyde, 9-phenanthrenecarboxaldehyde and fluorencarboxaldehyde; a heterocyclic aldehyde, selected from the group consisting of furfural, 5-methylfurfural, 5-bromofurfural, 4-isopropylfurfural, 2-thiophenecarboxaldehyde, 5-methylthiophenecarboxaldehyde, 9-methoxythiophene-2-carboxaldehyde, 2- pyridinecarboxaldehyde, 3-pyridinecarboxaldehyde, 4-pyridinecarboxaldehyde, 1-ethylindole-3-carboxaldehyde, 1-methylindole-3-carboxaldehyde, 1-methyl-2-phenylindole-3-carboxaldehyde, N-methylcarbazole-2-carboxaldehyde, N-ethyl-7-bromocarbazole-2-carboxaldehyde, N-(n-octyl)-7-nitrocarbazole-2-carboxaldehyde, benzofuran-2-carboxaldehyde, dibenzofuran-2-carboxaldehyde, pyrrole-2-aldehyde, N-methylpyrrole-2-aldehyde, N-phenylpyrrole-2-aldehyde, 3-methylpyrrole-2-aldehyde, 2-ethylpyrrole-5-aldehyde, benzothiazole-2-aldehyde, 6-methylbenzothiazole-2-aldehyde, 6-chlorobenzothiazole-2-aldehyde, 5-chlorobenzothiazole-2-aldehyde, 6-methoxybenzothiazole-2-aldehyde, 5,6-dichlorobenzothiazole-2-aldehyde, benzoselenazole-2-aldehyde, 6-methoxybenzoselenazole-2-aldehyde, 2,4-dimethylpyrrole-2-aldehyde, 4,6-dichloropyrimidine-5-carboxaldehyde, 2-formyl-4,6-dimethylpyrimidine, quinoline-2-aldehyde, acridine-10-aldehyde, 2,4-diphenyl-5,6,7-hexahydrobenzopyran-8-carboxaldehyde, and 2,4-diphenyl-6-methyl-5,6,7-pentahydrobenzopyran-8-carboxaldehyde; an aromatic nitroso compound selected from the group consisting of p-dimethylaminonitrosobenzene, p-diethylaminonitrosobenzene, p-methylnitroxobenzene (p-nitrosotoluene), p-nitronitrosobenzene, o-nitronitrosobenzene, and 3-nitroso-2-nitrotoluene; or a heterocyclic nitroso compound selected from the group consisting of 3-nitrosoindole, 2-methyl-3-nitrosoindole (3-nitrosomethyl-ketol), 3-nitroso-2-phenylindole and the like, and n is an integer of 2 or 3.

2. A styryl-like compound according to claim 1, wherein the alkyl group for R has 1 to 8 carbon atoms.

3. A styryl-like compound according to claim 2, wherein said alkyl group is methyl.

4. A styryl-like compound according to claim 1, wherein R represents phenyl.

5. A styryl-like compound according to claim 1, wherein R represents methyl and n is a value of 2.

6. A styryl-like compound according to claim 1, wherein R represents phenyl and n is a value of 2.

7. A styryl-like compound according to claim 1, wherein $R_3$ is hydrogen, Y is O, Z is an alkylene radical of 2 to 4 carbon atoms, with or without alkyl substituents, necessary for forming a ring structure together with

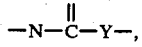

and A is aromatic aldehyde.

8. A styryl-like compound according to claim 7, wherein Z is $-CH_2-CH_2-$.

9. A styryl-like compound according to claim 8, wherein A is an aromatic aldehyde selected from the group consisting of p-anisaldehyde, p-dimethylaminocinnamaldehyde, p-dimethylamino-benzaldehyde, p-acetylamino-benzaldehyde, p-anisbenzaldehyde, p-tolylaldehyde, p-bromo-benzaldehyde, p-chloro-benzaldehyde, p-di-n-butylamino-benzaldehyde, 3,4-dimethoxy-benzaldehyde.

* * * * *